United States Patent [19]
Kusunoki et al.

[11] Patent Number: 5,876,959
[45] Date of Patent: Mar. 2, 1999

[54] METHOD FOR TESTING INFECTIOUS DISEASE CAUSING MICROORGANISMS

[75] Inventors: Shin-ichiro Kusunoki, Tokyo; Jun-ichiro Arai, Tsukuba-shi, both of Japan

[73] Assignee: Daikin Industries, Ltd., Japan

[21] Appl. No.: 638,851

[22] Filed: Apr. 29, 1996

Related U.S. Application Data

[63] Continuation of Ser. No. 211,160, filed as PCT/JP93/01016 Jul. 21, 1993, abandoned.

[30] Foreign Application Priority Data

Jul. 22, 1992 [JP] Japan .................................. 4-194340

[51] Int. Cl.[6] ....................................................... C12Q 1/04
[52] U.S. Cl. .................................. 435/34; 435/39; 435/40
[58] Field of Search .................................... 435/4, 34, 39, 435/40, 288.2, 293, 807, 817; 422/79

[56] References Cited

U.S. PATENT DOCUMENTS

| | | | |
|---|---|---|---|
| 3,957,583 | 5/1976 | Gibson | 195/103.5 R |
| 4,220,715 | 9/1980 | Ahnell | 435/34 |
| 4,246,343 | 1/1981 | Wilkins et al. | 435/32 |
| 4,288,543 | 9/1981 | Sielaff et al. | 435/34 |
| 4,311,794 | 1/1982 | Melnick et al. | 435/32 |
| 4,321,322 | 3/1982 | Ahnell | 435/34 |
| 4,350,763 | 9/1982 | Suzuki | 435/29 |
| 4,861,709 | 8/1989 | Ulitzur et al. | 435/6 |
| 5,160,604 | 11/1992 | Nakamura | 210/85 |

FOREIGN PATENT DOCUMENTS

| | | |
|---|---|---|
| 0509791A1 | 10/1992 | European Pat. Off. . |
| 295509 | 11/1991 | German Dem. Rep. . |
| 53-99379 | 8/1978 | Japan . |
| 5399379 | 8/1978 | Japan . |
| 56-140898 | 4/1981 | Japan . |
| 56140898 | 11/1981 | Japan . |
| A-01222767 | 9/1989 | Japan . |
| 3198767 | 12/1989 | Japan . |
| 3-198767 | 8/1991 | Japan . |
| WO 90/03441 | 4/1990 | WIPO . |

OTHER PUBLICATIONS

WPI/Derwent Abstract 89–303650, Figures 1–7, corresponds to JP–A–01222767 listed above.

*Primary Examiner*—Ralph Gitomer
*Attorney, Agent, or Firm*—Beveridge, DeGrandi, Weilacher & Young, LLP

[57] ABSTRACT

A method for detecting, identifying and measuring infectious disease causing microorganisms is described. The method utilizes a plural medium arrangement in which a test liquid containing a microorganism is simultaneously introduced. Different media are utilized for the plural medium arrangement and at least one of the media can contain a respiration inhibiting material and/or other reagents such as antibiotics. Dissolved oxygen measurements of the media are taken as a measurement of microorganism respiration. Oxygen electrode signals within different media are compared and differential respiration variation rates are determined and identification signals produced. The identification signal resulting from the multiple respiration rate determinations is compared with known values to identify and measure the microorganism. The drug sensitivity of a microorganism is also judged when at least one of the media contains a drug for which the sensitivity of microorganism is to be determined.

9 Claims, 3 Drawing Sheets

METHOD FOR TESTING INFECTIOUS DISEASE CAUSING MICROORGANISMS

This application is a continuation of U.S. patent application Ser. No. 08/211,160 filed Apr. 4, 1994, now abandoned, which was filed as PCT/JP93/01016 on Jul. 21, 1993.

TECHNICAL FIELD

This present invention relates to an infectious disease inspection method and apparatus, and, more particularly, this present invention relates to a method and apparatus for inspecting for an infectious disease in urine and the like.

BACKGROUND ART

From the past, various methods for detecting microorganisms existing within urine and the like are proposed as methods for inspecting infectious disease of urine and the like. These methods are as follows, for example.

(1) a method for recognizing colonies on an agar medium with the naked eye, after deposition of urine and the like on the agar medium, (2) a method for coloring micro-organisms in urine and the like, and for measuring a number of colored micro-organisms using a microscope, (3) a method for measuring the turbidity of a medium following multiplication of micro-organisms using a light intensity measurement, after deposition of urine and the like on the medium, (4) a method for using $C^{14}$ labelled compound as a nutritive source for micro-organisms in urine and the like, (5) a method for radiating infrared to urine and the like, and for measuring the absorption quantity of infrared based upon transmitted infrared intensity, and (6) a method for detecting bioluminescence.

When the method (1) is employed, since a condition for generating colonies on the agar medium should continuously be maintained, disadvantages arise in that the operation required for maintaining the condition is remarkably complicated, and in that it takes a remarkably long time period for the colonies to be recognized by the naked eye.

When the method (2) is employed, it is not possible to distinguish between living micro-organisms and non-living micro-organisms. Consequently, disadvantages arise in that the detection accuracy is lowered, and in that the operation becomes extremely complicated because of the number of colored micro-organisms within a visual field of the microscope.

When the method (3) is employed, since detection with high accuracy cannot be performed until the micro-organisms multiply to some degree, a disadvantage arises in that a minimum time period of about several hours to one day is necessary.

When the method (4) is employed, a disadvantage arises in that a radioactive material utilizing facility is necessary so as to extremely limit the places in which it is possible to perform the inspection.

When the method (5) is employed, since detection time varies greatly depending upon the species of microorganism, a disadvantage arises in that the detection result cannot be obtained with accuracy when the detection time is not determined accurately.

When the method (6) is employed, a disadvantage arises in that the operation becomes extremely complicated such that it is necessary to provide the appropriate set up for providing sufficient bioluminescence, and it is necessary to eliminate the influence of disturbance light, and the like.

Further, methods are proposed for measuring the number of living micro-organisms in a liquid provided for measurement by measuring the dissolved oxygen quantity which is caused by the respiration of micro-organisms (refer to laid-open publications of Tokukaihei 3-198767 and Tokukaisho 56-140898). But, both of these methods only make it possible to measure the number of micro-organisms, and the identification of a species of micro-organism and the, judgement of drug sensitivity and the like are impossible to be performed by both of these methods. Therefore, while both methods can be applied for judging the degree of infection of micro-organisms, identification of the species of the micro-organism and judgement of the drug sensitivity are performed by other methods. Both methods are quite insufficient for infectious disease inspection method for clinical examinations which strongly demand simpleness of operation and rapidity. Furthermore, since it is an extremely rare occurrence (actually, it is a scarce occurrence) that only the tested micro-organism respirates in the liquid provided for measurement in the clinical examination, the measurement is also influenced by the respiration of other living bodies. Thus, a disadvantage arises in that the measurement accuracy is lowered by the respiration of these other organisms.

DISCLOSURE OF THE INVENTION

The present invention was made to solve the above-mentioned problems.

It is an object of the present invention to supply an infectious disease inspection method and apparatus which can easily perform a measurement as to the number of a living micro-organism in a liquid provided for measurement, and perform identification judgement of the species of micro-organism and/or a judgement of drug sensitivity. A method of determining antibacterial drug sensitivity is described in U.S. Pat. No. 5,564,165.

To perform the object above-mentioned, an infectious disease inspection method according to the invention includes providing respiration interfering material in at least a part of a plural medium arrangement which includes mediums that are different from one another. The method further includes providing oxygen electrodes each corresponding to each of the mediums in the plural medium arrangement, supplying a liquid suited for measurement to the plural mediums simultaneously, detecting dissolved oxygen quantities with corresponding oxygen electrodes, each dissolved oxygen quantity being regulated by a condition of the liquid suited for measurement in each medium, and identifying a species of micro-organism in the liquid suited for measurement based upon output signals from the plural oxygen electrodes.

The infectious disease inspection method of the present invention also includes judging the drug sensitivity of a micro-organism in the liquid suited for measurement based upon the output signals from the plural oxygen electrodes, instead of or in addition to the identification of the species of the micro-organism.

The present invention also features an infectious disease inspection apparatus which includes a means for receiving a liquid suited for measurement, a plural medium arrangement which includes mediums that are different from one another and in at least a part of which there exists a material for interfering with respiration, passages for the measurement liquid with each passage communicating the means for receiving the measurement liquid and each medium, oxygen electrodes each corresponding to mediums of the plural medium arrangement, and output terminal means each for supplying output electrical signal from each oxygen electrode to a signal processing means.

When the infectious disease inspection method of the present invention is employed, respiration or oxygen consumption of a living body in the liquid provided for measurement is limited to that of a micro-organism, because respiration interfering material exists in at least a part of the plural medium arrangement and because the oxygen electrodes each corresponding to each of the plural mediums are provided. Respiration or oxygen consumption of the micro-organism and that of an non-micro-organism are measured simultaneously, and identification of species of micro-organism in the liquid objected for measurement is performed based upon the output electrical signals from the plural oxygen electrodes corresponding to the respiration or oxygen consumption. Because the liquid provided for measurement is supplied to the plural medium simultaneously, and because each dissolved oxygen quantity is detected with a corresponding oxygen electrode, each dissolved oxygen quantity is regulated by the condition of the liquid provided for measurement in each medium. Therefore, a species of micro-organism existing in the liquid provided for measurement is identified accurately within a short time period by preparing the medium to correspond to a species of micro-organism considered to possibly exist in the liquid objected for measurement. The quantity of the micro-organism is measured based upon a variation in the values of the output electrical signals from the oxygen electrodes.

In the infectious disease inspection method of the present invention, a drug's effectiveness for providing medical treatment to an infectious disease is judged accurately and within a short time period, because judging drug sensitivity of a micro-organism in the liquid provided for measurement is performed based upon the output signals from the plural oxygen electrodes, instead of or in addition to the identification of species of microorganism. The infectious disease inspection method is a method suitable for clinical examination in which rapidity and accuracy are required.

When the infectious disease inspection apparatus of the present invention is employed, after the liquid provided for measurement is received by the means for receiving liquid provided for measurement, the liquid provided for measurement is supplied to the plural medium arrangement containing mediums which are different from one another and in at least a part of which there exists a material for interfering with respiration, and then through the passages for the liquid provided for measurement. And, each of the electrical signals corresponding to the respiration or oxygen consumption, determined based upon adaptability and the like in the medium, is output from each oxygen electrode. By supplying these electrical signals to the signal processing means through the output terminal means, an identification result of the species of microorganism existing in the liquid objected for measurement and/or a judgement result of drug sensitivity is provided. Therefore, by previously preparing a medium in correspondence to a species of micro-organism possibly existing in the liquid provided for measurement, the species of microorganism existing in the liquid provided for measurement is identified accurately within a short time period, and drug sensitivity is also accurately judged. The quantity of micro-organism is measured based upon the variation values of the output electrical signals from the oxygen electrodes.

BEST FORMS OF CARRYING OUT THE INVENTION

Referring to the attached drawings, we explain the invention in detail.

Figure 1:
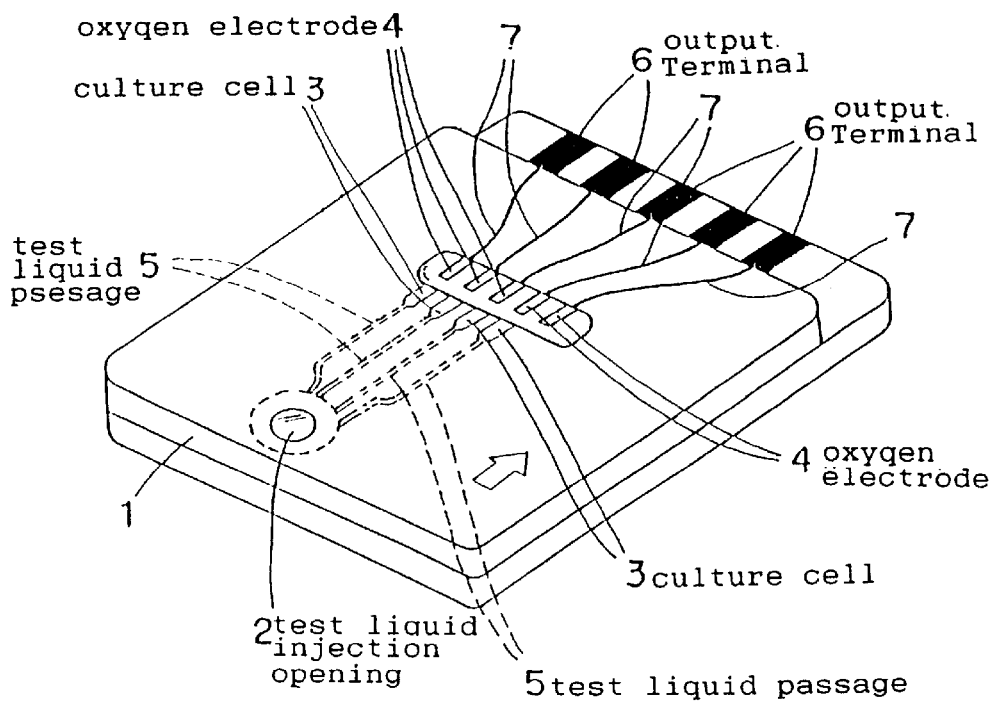
FIG. 1 is a schematical view illustrating an embodiment of an infectious disease inspection apparatus according to the present invention.

FIG. 1 is a schematic view illustrating an infectious disease inspection apparatus according to the present invention. A test liquid injection opening 2 is formed at a predetermined position of a base member 1 having predetermined shape. Plural culture cells 3 housing plural medium, respectively, are formed at predetermined positions of the base member 1, the mediums being different from one another. Oxygen electrodes 4 are disposed, each corresponding to each culture cell 3. And, test liquid passages 5 for communicating the test liquid injection opening 2 and each culture cell 3, are formed. Plural output terminals 6 are disposed at predetermined edge-ward positions of the base member 1, and each output terminal 6 is connected to the corresponding oxygen electrode 4 through a wire 7. Respiration interfering material exists in at least a part of the plural medium arrangement.

Figure 2:
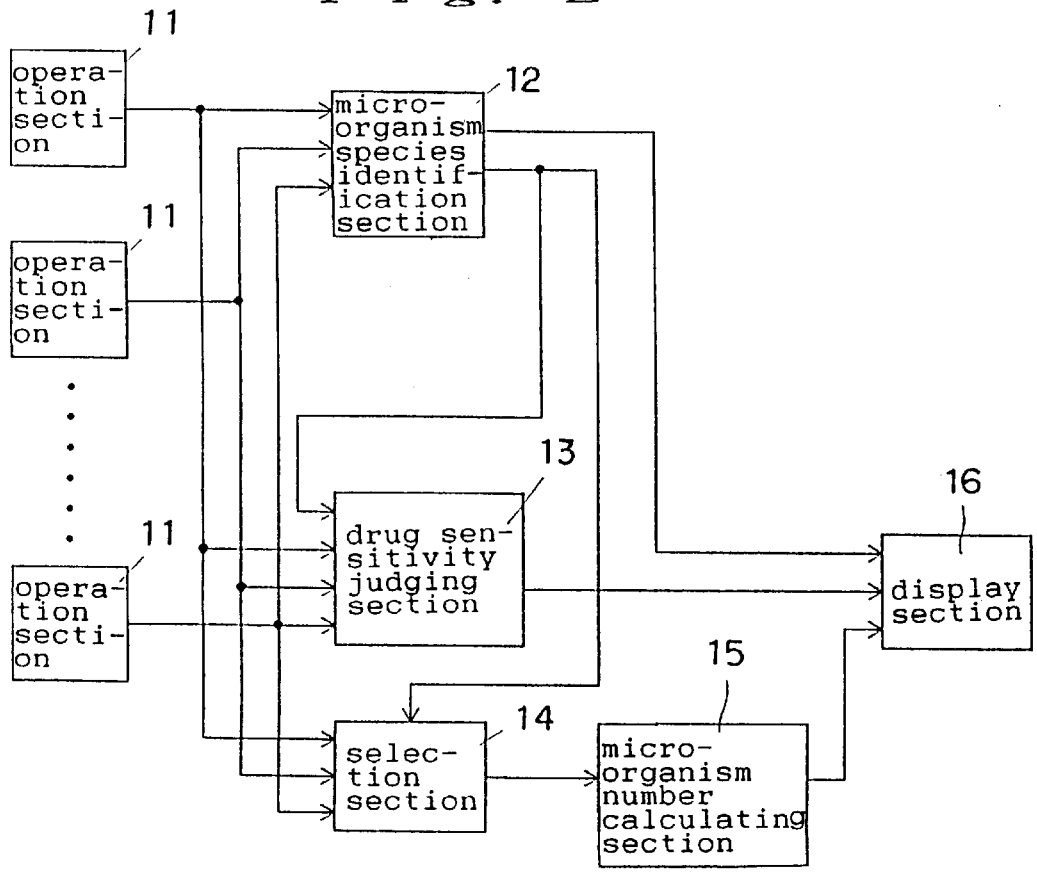
FIG. 2 is a block diagram schematically illustrating an arrangement of a signal processing section for counting a micro-organism, for identifying a species of micro-organism, and for judging drug sensitivity based upon output electrical signals from the infectious disease inspection apparatus having the arrangement in FIG. 1.

FIG. 2 is a block diagram schematically illustrating an arrangement of a signal processing section for the counting of a micro-organism, for identifying of a species of micro-organism, and for judging the drug sensitivity based upon output electrical signals from the infectious disease inspection apparatus having the arrangement in FIG. 1. The signal processing section includes an operation sections 11 for carrying out predetermined processing (for example, amplifying and comparing processing, differentiating and comparing processing and the like) to output signals from the oxygen electrodes 4 so as to obtain binary data or multivalued data, the operation sections 11 being provided in correspondence to the plural output terminals 6, a micro-organism species identification section 12 for identifying a species of micro-organism existing in the test liquid based upon data output from all operation sections 11, a drug sensitivity judging section 13 for judging drug sensitivity based upon the identification result and/or data output from all operation sections 11, a selection section 14 for selecting output signals from a corresponding oxygen electrode 4 based upon the identification result output from the micro-organism species identification section 12, micro-organism number calculating section 15 for calculating a number of micro-organisms based upon a timely variation rate of the selected output signal, and a display section 16 for visually displaying the identification result, judgement result and calculation result.

Function of the infectious disease inspection apparatus having the above-mentioned arrangement is as follows.

When a test liquid provided for inspection of infectious disease is injected in the test liquid injection opening 2 under the condition that the infectious apparatus illustrated in FIG. 1 is connected to the signal processing section illustrated in FIG. 2, the injected test liquid arrives to each culture cell 3 almost simultaneously through the plural test liquid passages 5. Since each culture cell 3 is previously provided with a selection medium, respiration interfering material, and a reagent such as antibiotics and the like, survivable culture cells 3 and non-survivable culture cells 3 are determined in correspondence to species of micro-organism in the test liquid. Since in the survivable culture cells 3 in which micro-organism can survive, the dissolved oxygen is consumed by the respiration of micro-organism, electric signals corresponding to the decrease of of the dissolved oxygen are output from corresponding oxygen electrodes 4. On the contrary, since the dissolved oxygen is not consumed in the non-survivable culture cells 3, electric signals corresponding to the condition that the dissolved oxygen is not decreased, are output from corresponding oxygen electrodes 4.

These electrical signals output from each oxygen electrode 4 are supplied to the operation sections 11 through the output terminals, and binary data or multivalued data are obtained by performing predetermined processing. Data output from all operation sections 11 are supplied to the micro-organism species identification section 12 and the drug sensitivity judging section 13. Species of microorganism existing in the test liquid is identified, and drug sensitivity is judged based upon a combination of this data. Further, the output signals from corresponding oxygen electrodes 4 are selected by the selection section 14 based upon the identification result from the micro-organism species identification section 12, the number of a micro-organism is calculated by the micro-organism number calculating section 15 based upon a timely variation rate of the selected output signal and the like.

The identification result, judgement result and calculation result are visually displayed by the display section 16.

As is apparent from the foregoing description, identification of species of a micro-organism and a judgement of drug sensitivity are automatically carried out so as to perform the infectious disease inspection, by only injecting the test liquid in the test liquid injection opening 2 by an operator. Further, the degree of infection is measured because a calculation as to the number of a micro-organism is also carried out.

Specific Example

Figure 3:
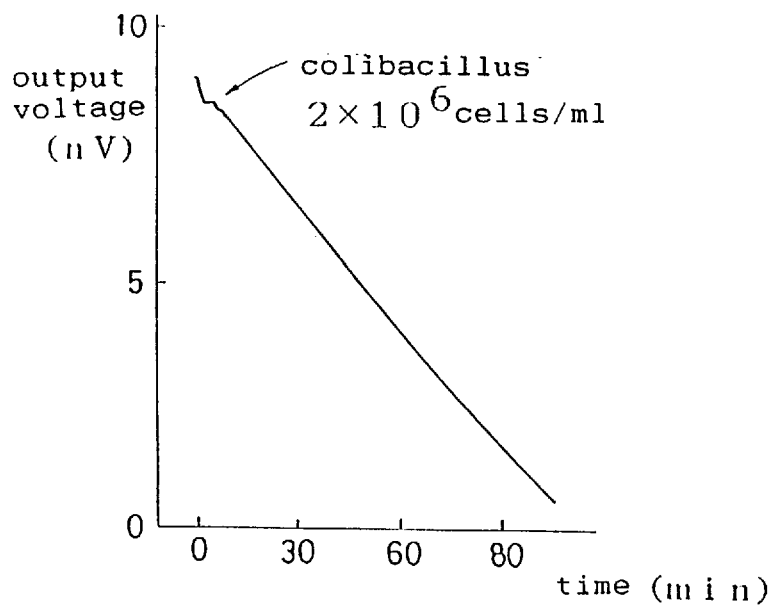
FIG. 3 is a graph illustrating variation with the passage of time of output voltage (nV) from the oxygen electrode, when the micro-organism is colibacillus ($2 \times 10^6$ cells/ml)
Figure 4:
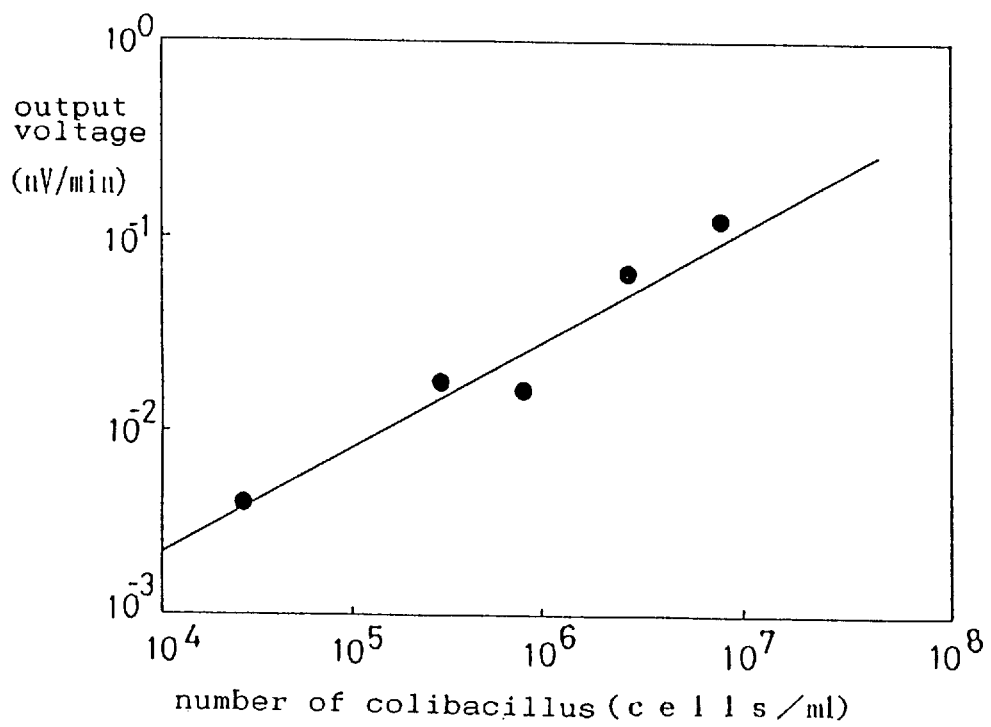
FIG. 4 is a graph illustrating the variation of a time differential value (nV/min.) of the output voltage from the oxygen electrode corresponding to a number of colibacillus.

L-bullous (medium having a composition of peptone, meat extract, yeast extract, and grape sugar) is used as a first medium. L-bullous to which is added Bile Salts No. 3 (Difsco) and crystal violet represents a second medium which is used as a gram-negative rod-shaped bacteria selection medium. Staphylococcus (gram-positive coccus) and colibacillus (gram-negative rod-shaped bacteria) are used as the micro-organisms. Each micro-organism and chosen medium are housed and sealed in a test cell of 2 ml, and dissolved oxygen quantities are measured using the oxygen electrodes with the microorganism and medium being stirred. FIG. 3 is a graph illustrating variation with the passage of time of output voltage (nV) from the oxygen electrode, when the micro-organism is colibacillus ($2 \times 10^6$ cells/ml) . From FIG. 3, it is understood that dissolved oxygen is decreased by respiration of colibacillus. FIG. 4 is a graph illustrating variation of a time differential value (nV/min.) of the output voltage from the oxygen electrode corresponding to a number of colibacillus. From FIG. 4, it is understood that the time differential value increases following the increase in the number of colibacillus.

Figure 5A:
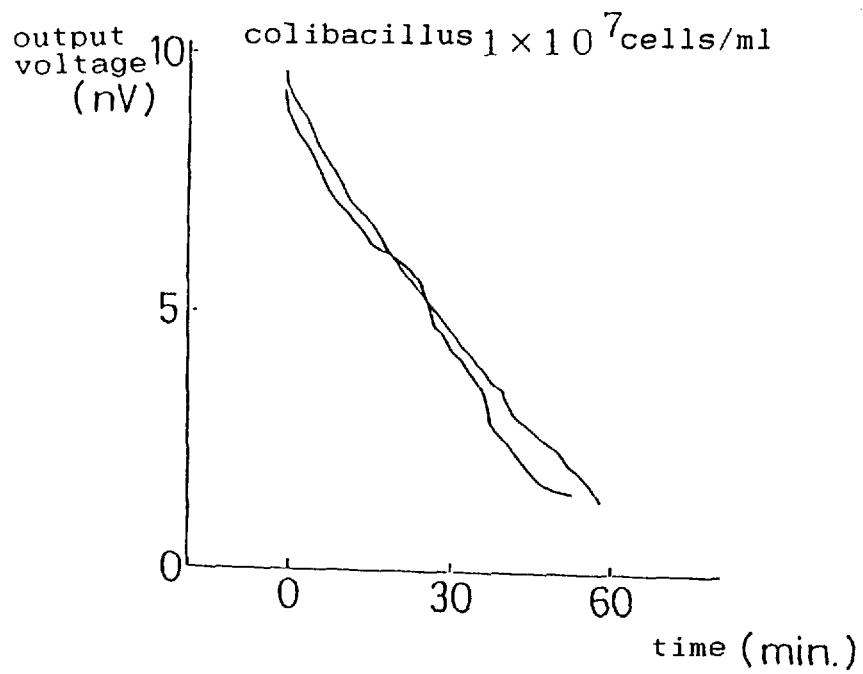
FIG. 5A and FIG. 5B are graphs illustrating variation with the passage of time of output voltages from the oxygen electrodes, when colibacillus and staphylococcus are added to the medium, respectively.
Figure 5B:
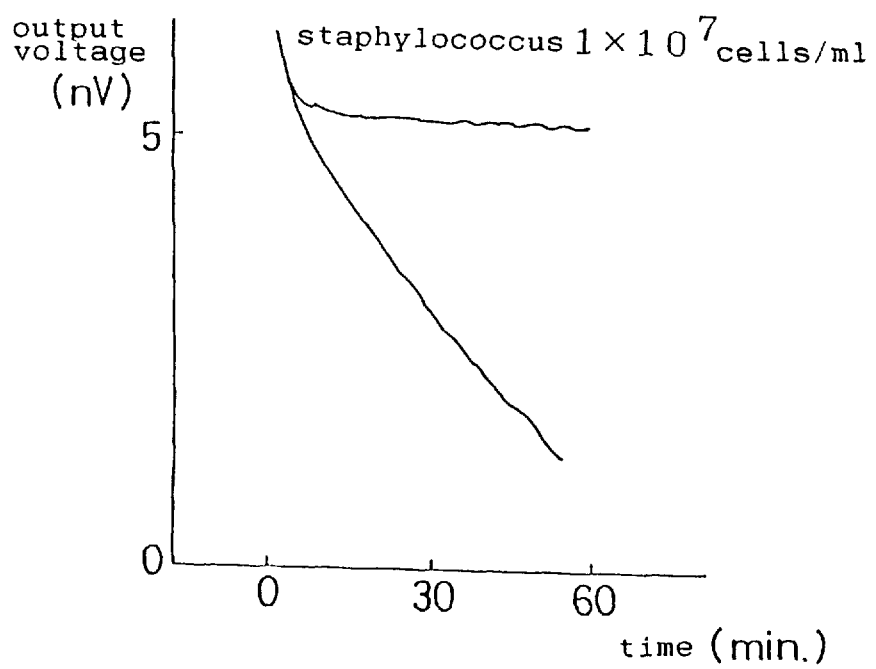

When the micro-organism is colibacillus, a similar output to one another is obtained in each medium. However, when the micro-organism is staphylococcus, the variation rate of output becomes an extremely low value in the gram-negative rod-shape bacteria selection medium such that the variation rate is 0–20 with respect to that in the L-bullous example. And, it is apparent from FIG. 5A and FIG. 5B, which illustrate a variation with the passage of time of output voltages (nV) from the oxygen electrodes when colibacillus and staphylococcus are added to the medium, respectively. Consequently, by comparing both outputs in two species of medium to one another, the micro-organism is identified as to whether it is gram-positive or gram-negative, and drug sensitivity is judged based upon the identification result. That is, since a micro-organism is generally determined by its drug sensitivity to a specific drug depending upon whether it is gram-positive or gram-negative, a disadvantage can securely be eliminated that a drug having no effect is dosed to an infectious disease patient by judging drug sensitivity based upon the above-mentioned identification result. Further, a number of the micro-organism is calculated by carrying out a predetermined operation which is determined by the species of micro-organism, based upon the output in L-bullous, for example.

In the above-mentioned specific example, it is only judged whether the micro-organism is gram-positive or gram-negative. When another medium is/are employed so as to obtain output similar to the above-mentioned manner, more minute identification of micro-organism is performed, and useful judgement of drug sensitivity for selecting more adequate drug is also performed. For example, when citric acid medium is employed, judgement can be performed whether or not vitamin, amino acid and the like are needed for utilizing an organic compound included in the citric acid medium as a carbon source and energy source. Further, malonic acid medium, M70 medium Kauffmann-Petersen medium and the like are applicable. Especially, as to the M70 medium, it can be judged whether or not a corresponding organic compound can be utilized as a carbon source or an energy source, by suitably selecting the organic compound which is added to the medium. Therefore, identification accuracy of species of microorganism is improved by preparing plural M70 mediums with each M70 medium having added to it a different organic compound. Of course, using this technique judgement accuracy of drug sensitivity can also be improved.

Possibility of Industrial Utilization

The present invention identifies species of microorganism in a liquid objected for measurement in a short time period based upon the output voltages from the oxygen electrodes, each oxygen electrode corresponding to each of a plurality of mediums. Therefore, a drug and the like having sensitivity is rapidly selected based upon the identification result. Consequently, the present invention is useful for suppressing activity and the like of harmful species of micro-organisms in a living body system, reaction system and the like.

What is claimed is:

1. A method for identifying a species of microorganism in a test liquid in the presence of non-microorganism cell respiration, comprising:

supplying a test liquid containing the species of microorganism such that the test liquid is received simultaneously within a plurality of culture cells containing different culture mediums to form different combinations of test liquid containing the species of microorganism and the different culture mediums wherein each culture cell is provided with an oxygen electrode that contacts the test liquid and produces an output signal indicating the dissolved oxygen quantity within the combinations and wherein at least one of said combinations contains a respiration interfering material;

detecting differences in dissolved oxygen quantities in the different combinations within said culture cells with the oxygen electrodes respectively corresponding to said culture cells, and with the differences in dissolved oxygen quantities being due to differences in oxygen consumption by the species of microorganism in the combinations;

comparing output signals from said oxygen electrodes, correlating said output signals with stored information and identifying a species of organism in the test liquid based upon a comparison of said output signals and a correlation of said output signals with stored information.

2. The method as set forth in claim 1, wherein at least one medium contains an antibiotic, said method further comprising the step of;

determining drug sensitivity of the species of microorganism in the test liquid based upon a comparison of output signals including the output signal from the dissolved oxygen electrode contacting one of the combinations that includes the medium containing the antibiotic.

3. The method as recited in claim 2, further comprising the step of;

calculating a number of microorganisms of said species of microorganism per unit volume of the test liquid based upon measuring a time based variation in oxygen consumption of the identified species as detected by one of said oxygen electrodes in contact with one of the combinations of test liquid containing microorganisms and medium contained in a selected one of said culture cells and comparing the time based variation with stored information as to an oxygen consumption rate for the identified species of microorganism.

4. The method as recited in claim 1, further comprising calculating a number of microorganisms of said species of microorganism per unit volume of the test liquid based upon a time based variation in oxygen consumption of the identified species as detected by one of said oxygen electrodes in contact with the combination of test liquid and medium contained in a selected one of said culture cells.

5. A method for identifying a species of of microorganism in a test liquid in the presence of non-microorganism cell respiration, comprising supplying a test liquid to an opening formed in a structural member such that the test liquid is fed simultaneously into a plurality of culture cells formed in the structural member, said culture cells containing different culture mediums such that, upon contact of the test liquid with said mediums in said culture cells, dissolved oxygen is detected with oxygen electrodes corresponding respectively to said culture cells; and identifying a species of microorganism in the liquid based upon a comparison of output signals from said oxygen electrodes, which output signals correspond with a level of dissolved oxygen detected by said oxygen electrodes in said culture cells, and by correlating said output signals with stored information as to established attributes of a variety of different species subject to at least one medium which is in common with at least one of said mediums in said culture cells.

6. The method as recited in claim 5, wherein at least one medium contains an antibiotic, said method further comprising the step of;

determining drug sensitivity of the species of the microorganism in the test liquid based upon a comparison of signals, which signals being compared include a species identification signal corresponding to the identified species of microorganism in the test liquid as well as the output signals of said oxygen electrodes.

7. The method as recited in claim 6, further comprising calculating a number of microorganisms of said species of microorganism per unit volume of the test liquid based upon a determination of a time based variation in oxygen consumption of the identified species as detected by one of said oxygen electrodes in contact with the combination of test liquid and medium contained in a selected one of said culture cells and a comparison of the time based variation with stored information as to an oxygen consumption rate for the identified species of microorganism.

8. The method as recited in claim 5, further comprising calculating a number of microorganisms of said species of microorganism per unit volume of the test liquid based upon a determination of a time based variation in oxygen consumption of the identified species as detected by one of said oxygen electrodes in contact with the combination of test liquid and medium contained in a selected one of said culture cells and a comparison of the time based variation with stored information as to oxygen consumption for the identified species of microorganism.

9. A method for identifying a species of microorganism in a test liquid in the presence of non-microorganism cell respiration, comprising:

supplying a test liquid containing a species of microorganism such that the test liquid is simultaneously received within a plurality of different culture mediums contained in respective culture cells to form different combinations of test liquid and mediums and wherein at least one of said combinations contains a respiration interfering material;

detecting, with oxygen electrodes, differences in dissolved oxygen quantities within the different combinations of the test liquid and mediums contained within said culture cells, and said oxygen electrodes corresponding, respectively, with said culture cells and with the differences in dissolved oxygen quantities being due to differences in oxygen consumption between the species in the test liquid and the different mediums in the combinations;

comparing dissolved oxygen quantities detected in said culture cells by said oxygen electrodes, correlating the dissolved oxygen quantities detected by said oxygen electrodes with reference to stored information, and identifying a species of organism in the test liquid based upon a comparison of said output signals and a correlation of said output signals with stored information.

* * * * *